United States Patent [19]

Svensson

[11] 3,994,286

[45] Nov. 30, 1976

[54] CIRCUIT ARRANGEMENT FOR THE PROCESSING OF PHYSIOLOGICAL MEASURING SIGNALS

[75] Inventor: Clas Svensson, Akersberga, Sweden

[73] Assignee: Siemens Aktiengesellschaft, Erlangen, Germany

[22] Filed: June 19, 1975

[21] Appl. No.: 588,466

[30] Foreign Application Priority Data

June 21, 1974 Germany.............................. 2429954

[52] U.S. Cl. ............................................. 128/2.06 B
[51] Int. Cl.$^2$ ............................................. A61B 5/04
[58] Field of Search ................... 128/2.06 B, 2.06 G, 128/2.06 R, 2.1 R

[56] References Cited

UNITED STATES PATENTS

| | | | |
|---|---|---|---|
| 3,811,428 | 5/1974 | Van Horn et al. .............. | 128/2.06 B |
| 3,868,948 | 3/1975 | Graetz............................ | 128/2.06 B |

OTHER PUBLICATIONS

Huntsman et al. "IEEE Transactions on Bio-Medical Engineering", vol. 18, No. 4, July, 1971, pp. 301–304.

Primary Examiner—William E. Kamm
Attorney, Agent, or Firm—Haseltine, Lake & Waters

[57] ABSTRACT

A circuit arrangement for the processing of physiological measuring signals, in which there is provided a plurality of input amplifiers each having a positive and a negative input, whose output signals control a signal reproducing arrangement, and which are each connected to a collector electrode. Connected to the positive inputs of the input amplifier are the collector electrodes for the signals, and that resistors are located between the negative inputs and the outputs of the input amplifiers, the negative inputs being connected across the resistors with a common potential junction, and that the two inputs of a differential amplifier are connected to the outputs of respectively two input amplifiers, the output signal of the differential amplifier controlling the signal reproducing arrangement.

4 Claims, 5 Drawing Figures

3,994,286

CIRCUIT ARRANGEMENT FOR THE PROCESSING OF PHYSIOLOGICAL MEASURING SIGNALS

FIELD OF THE INVENTION

The present invention relates to a circuit arrangement for the processing of physiological measuring signals, in which there is provided a plurality of input amplifiers each having a positive and a negative input, whose output signals control a signal reproducing arrangement, and which are each connected to an output or collector electrode.

DISCUSSION OF THE PRIOR ART

A known circuit arrangement of the above-mentioned type is utilized in an electrocardiograph. In the known electrocardiographs, all of the voltages which are branched or tapped off from a patient are measured in comparison with a voltage which is tapped off from a reference electrode. In that manner, there is achieved that interference signals (static hum) which cause the potential of the entire body to deviate from zero, are extensively eliminated. The exclusion of these static signals is effectuated in that the input amplifiers are constructed as differential amplifiers which amplify the difference between their present input signal and the reference signal, and wherein the static hum is also impressed or superimposed on the input signal as an in-phase signal.

A satisfactory operating effect is afforded in the known electrocardiographs only when the input amplifiers all possess the same definite amplification and when, in particular, the components of these amplifiers evidence relatively narrow tolerances so that, upon subtraction of two equally large input signals of a differential amplifier, there is obtained the output signal zero with a high degree of exactness. A disadvantage in the known electrocardiographs lies in that the circuit requirements or expenditures for the input amplifiers are quite considerable.

SUMMARY OF THE INVENTION

Accordingly, it is an object of the present invention to provide a circuit arrangement of the above-mentioned type, in which the input circuit is essentially more simply constructed than those in the current state of the technology wherein, particularly in this circuit, utilization is made of operational amplifiers, and in which tolerances in the components which are within relatively wide limits will not adversely affect the in-phase suppression, meaning the suppression of interference or static signals.

The foregoing object is inventively achieved in that connected to the positive inputs of the input amplifier are the collector electrodes for the signals, and that resistors are located between the negative inputs and the outputs of the input amplifiers, the negative inputs being connected across the resistors with a common potential junction, and that the two inputs of a differential amplifier are connected to the outputs of respectively two input amplifiers, the output signal of the differential amplifier controlling the signal reproducing arrangement. In the inventive circuit arrangement, each input amplifier may be constructed of a commercially available operational amplifier which is wired with two additional resistors. The construction of an input amplifier is thus appreciably simplified in comparison with those in the current state of the art. The tolerances of these resistors and the amplification of the input amplifiers exert no effect on the extent of the in-phase suppression. The suppression is carried out by means of a differential amplifier which is connected to the input amplifiers. The in-phase suppression within the entire arrangement, however, is dependent upon the internal in-phase suppression of the amplifiers in the input circuit. The in-phase signals are not amplified by means of the input amplifiers, whereas the differential signals between two electrodes appear amplified at the outputs of the input amplifiers, so that tolerances of the thereto connected differential amplifier has an influence on the in-phase suppression reduced by the amplification factor.

BRIEF DESCRIPTION OF THE DRAWINGS

Further advantages and details of the invention may now be ascertained from the following description of an exemplary embodiment thereof, taken in conjunction with the accompanying drawings; in which.

DETAILED DESCRIPTION

Figure 1:
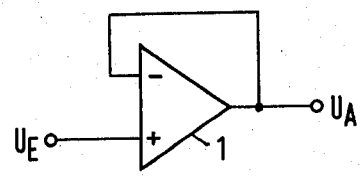
FIGS. 1 through 4 each respectively discloses a circuit diagram for elucidating the present invention.

FIG. 1 illustrates an operational amplifier 1 in a voltage follower coupling, which possesses a high input impedance and a lower output impedance, as well as a high amplification in the no-feedback or back-coupled condition. The output voltage UA is equal to the input voltage UE.

Figure 2:
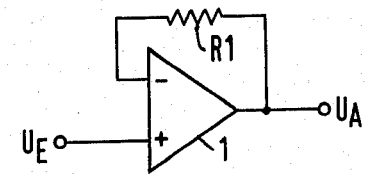

According to FIG. 2, a resistor R1 has been introduced in the feedback circuit. Inasmuch as the input impedance is very large, practically no current flows in the resistor R1 and so that this resistor will not influence the relationships whereby, also in this instance, the output voltage UA is equal to the input voltage UE.

Figure 3:
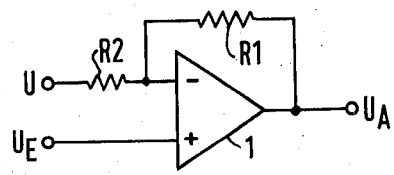

According to FIG. 3 a second resistor R2 is connected in series with the negative input of the operational amplifier 1. The free end of the resistor R2 assumes the voltage U = UE = UA when the voltage UE is applied to the positive input of the operational amplifier 1.

Figure 4:
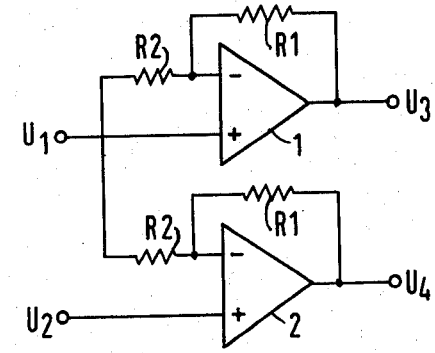

FIG. 4 illustrates a coupling of two amplifiers according to FIG. 3, in which the free ends of the resistors R2 are connected to each other. It is initially assumed that the two inputs U1 and U2 have the same voltage transmitted thereto, meaning, that U1 = U2 = UE. Since the two circuit halves are identical, no currents flow through the resistors R1 and R2, independently of the resistance values. The in-phase signal, which is transmitted to the two inputs U1 and U2, hereby again appears at the outputs of the operational amplifiers 1 and 2 in the form of voltages U3 and U4. For the case in which U1 = U2 = UE, it is thus valid that U3 = U4 = UE. The in-phase signal is thus not amplified by means of the circuit pursuant to FIG. 4.

When U1 is not equal to U2, the following pertains, due to the amplification of the differential signal:

$$U3 - U4 = (1 + \frac{R1}{R2}) \cdot (U1 - U2).$$

In summation, there may be determined in connection with the circuit according to FIG. 4, that an in-phase signal at the two inputs will again appear unchanged at the outputs, whereas the differential signal between the voltages at the two inputs will again appear at the output, amplified by the factor 1 + R1/R2. The circuit according to FIG. 4 forms the basis for the input circuit the electrocardiograph, as is shown in FIG. 5 of the drawings.

Figure 5:
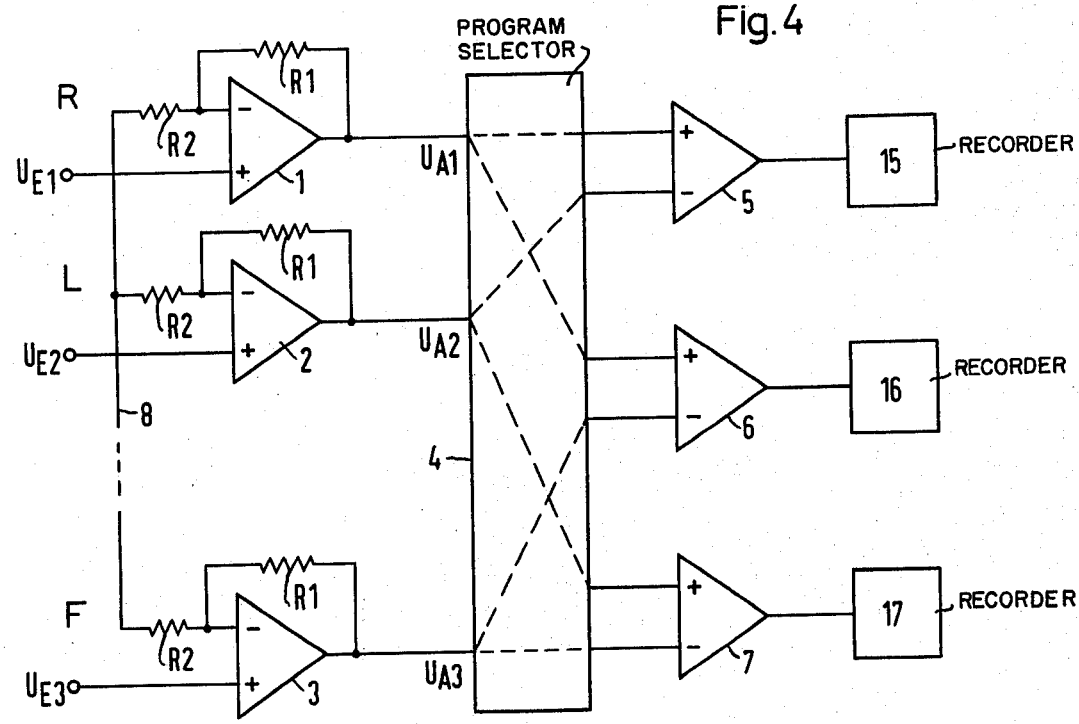
FIG. 5 is a circuit arrangement in accordance with the invention, which forms a component of an electrocardiograph.

FIG. 5 illustrates three operational amplifiers 1 through 3, which are interconnected pursuant to FIG. 4. Connected to the positive inputs of the operational amplifiers 1 through 3 are the branch or take-off electrodes R, L and F for the EKG, and interposed between the second inputs (negative-inputs) and the outputs of the operational amplifiers 1 through 3 are resistors R1. The negative-inputs of the operational amplifiers 1 through 3 are further connected, through resistors R2, with a common potential junction 8. The outputs of the operational amplifiers 1 through 3 are connected to a program selector 4, in which the inputs of the subsequently connected differential amplifiers 5 through 7 or connected to the outputs of the operational amplifiers 1 through 3. Thus, for example, the two inputs of the differential amplifier 5 are connected to the outputs of the operational amplifiers 1 and 2, and the two inputs of the differential amplifier 6 are connected to the outputs of the operational amplifiers 1 and 3. The program selector 4 thus connects the preprogrammed output pairs of the input amplifiers 1 through 3 with each of the thereto connected differential amplifiers 5 through 7. Connected between the outputs of the operational amplifiers 1 through 3 and the inputs of the program selector 5 can be suitable RC-elements for the elimination of direct-current voltages. The differential amplifiers 5 through 7 have EKG recorder installations 15 through 17 connected thereto. A recorder which may be utilized herein is described, for example, in Canadian Patent 513,848.

In the difference formation in the differential amplifiers 5 through 7, the in-phase signal (static hum) is eliminated, while the differential signal between two branch or take-off electrodes are detected in an amplified form. With respect to this differential signal, the following applies:

$$UAp - UAq = (1 + \frac{R1}{R2}) \cdot (UEp - UEq).$$

It is ascertained that the resistors R1 and R2, as well as the amplification of the operational amplifiers 1 through 3 do not influence the in-phase suppression. Consequently, relative large tolerances are permissible for these construction components. The in-phase signal is suppressed first in the differential amplifiers 5 through 7, which receive the transmitted EKG signal in an already amplified form (differential signal at their inputs). The tolerances in the differential amplifiers 5 through 7 thereby also exert only a relatively small effect on the in-phase suppression.

The number of the input circuits is not important to the present invention. In FIG. 5 there is illustrated, by means of the phantom lines, that this number may be further increased.

The invention is also particularly suitable, as described, to application in an electrocardiograph, but is also adapted for the processing of other physiological measuring signals which have an in-phase signal (static hum) superimposed thereon. Thus, the invention may be employed, for example, in the obtaining of an EEG.

While there has been shown what is considered to be the preferred embodiment of the invention, it will be obvious that modifications may be made which come within the scope of the disclosure of the specification.

What is claimed is:

1. In a circuit arrangement for the processing of physiological measuring signals, including a plurality of input amplifiers each having respectively a positive input and a negative input; a signal reproducing installation controlled by the output signals of said input amplifiers; and a take-off electrode connected to each said input amplifier, the improvement comprising: said take-off electrodes for said signals being connected to the positive inputs of said input amplifiers; first resistors being connected between said negative inputs and the outputs of said input amplifiers; second resistors being connected between said negative inputs and a common potential junction for the latter; differential amplifier means having two inputs connected to the outputs of at least two of said input amplifiers, said differential amplifier means having an output connected to said reproducing installation and providing an output signal for controlling said signal reproducing installation; said differential amplifier means comprising a plurality of differential amplifiers connected in series; and a program selector positioned between the outputs of said input amplifiers and the inputs of a plurality of said differential amplifiers for connecting pre-programmed output pairs of the input amplifiers to each of said differential amplifiers, said common potential junction being free of ground potential.

2. A circuit arrangement as claimed in claim 1, said take-off electrodes being connected to the positive inputs of said input amplifiers for application in an electrocardiograph.

3. A circuit arrangement as claimed in claim 1, said first resistors between the negative inputs and the outputs of said input amplifiers being equally large, and the second resistors between the negative inputs of said input amplifiers and said common potential junction being equally large.

4. A circuit arrangement as claimed in claim 1, said input amplifiers comprising operational amplifiers.

* * * * *